US012805782B2

(12) United States Patent
Karpenkop et al.

(10) Patent No.: US 12,805,782 B2
(45) Date of Patent: Nov. 24, 2026

(54) SENSOR INCLUDING ELECTRICALLY CONDUCTIVE MATERIAL CONTAINMENT ASSEMBLY

(71) Applicant: Covidien LP, Mansfield, MA (US)

(72) Inventors: Ido Karpenkop, Yavne (IL); Raz Levin, Tzur Hadassah (IL)

(73) Assignee: Covidien LP, Mansfield, MA (US)

( * ) Notice: Subject to any disclaimer, the term of this patent is extended or adjusted under 35 U.S.C. 154(b) by 841 days.

(21) Appl. No.: 18/005,090

(22) PCT Filed: Jun. 21, 2021

(86) PCT No.: PCT/US2021/038267

§ 371 (c)(1),
(2) Date: Jan. 11, 2023

(87) PCT Pub. No.: WO2022/015472

PCT Pub. Date: Jan. 20, 2022

(65) Prior Publication Data

US 2023/0337954 A1 Oct. 26, 2023

Related U.S. Application Data

(60) Provisional application No. 63/051,058, filed on Jul. 13, 2020.

(51) Int. Cl.
*A61B 5/256* (2021.01)
*A61B 5/00* (2006.01)
(Continued)

(52) U.S. Cl.
CPC .............. *A61B 5/257* (2021.01); *A61B 5/266* (2021.01); *A61B 5/6832* (2013.01)

(58) Field of Classification Search
CPC ........... A61B 5/25; A61B 5/282; A61B 5/266; A61B 5/257; A61B 5/259;
(Continued)

(56) References Cited

U.S. PATENT DOCUMENTS 3,942,517 A 3/1976 Bowles et al.
4,353,373 A 10/1982 Sessions et al.
(Continued)

FOREIGN PATENT DOCUMENTS

CN 209074607 U 7/2019
EP 0082728 A2 6/1983

OTHER PUBLICATIONS

International Preliminary Report on Patentability from International Application No. PCT/US2021/038267 dated Jan. 26, 2023, 10 pp.
(Continued)

*Primary Examiner* — Joseph A Stoklosa
*Assistant Examiner* — Brian M Antiskay
(74) *Attorney, Agent, or Firm* — Dymera IP, LLC

(57) ABSTRACT

In some examples, a medical sensor comprises a containment assembly and an electrode assembly having an electrode well. The containment assembly comprises a deformable housing configured to house an electrically conductive material and being formed with one or more apertures. The container assembly also comprises at least one membrane configured to cover at least one aperture of the one or more apertures to contain the electrically conductive material in the housing. Upon application of a sufficient force to the housing, the housing is configured to assume a deformed state in which the at least one membrane is configured to at least partially uncover the at least one aperture to enable the electrically conductive material to be released from the housing and into the electrode well through the at least one aperture.

20 Claims, 7 Drawing Sheets

(51) Int. Cl.
*A61B 5/257* (2021.01)
*A61B 5/266* (2021.01)

(58) Field of Classification Search
CPC ................ A61B 2562/125; A61B 5/28; A61B 2562/0217; A61B 2560/0412; A61B 5/6831; A61B 5/24; A61B 5/6804; A61B 5/6823; A61B 5/0006; A61B 5/6814; A61B 5/324; A61B 5/332; A61B 5/053; A61B 2560/0468; A61B 5/6803; A61B 2562/168
USPC .......................................... 600/372, 382–393
See application file for complete search history.

(56) References Cited

U.S. PATENT DOCUMENTS

| | | | | |
|---|---|---|---|---|
| 4,522,211 | A | 6/1985 | Bare et al. | |
| 4,526,176 | A * | 7/1985 | Bremer | A61B 5/251 600/397 |
| 4,928,690 | A * | 5/1990 | Heilman | A61B 5/6831 600/509 |
| 5,305,746 | A | 4/1994 | Fendrock | |
| 6,032,072 | A | 2/2000 | Greenwald et al. | |
| 6,240,323 | B1 | 5/2001 | Calenzo, Sr. et al. | |
| 6,874,621 | B2 | 4/2005 | Solosko et al. | |
| 9,162,045 | B2 | 10/2015 | Jones | |
| 9,220,436 | B2 | 12/2015 | Sandmore et al. | |
| 11,324,429 | B2 * | 5/2022 | Willis | A61B 5/291 |
| 11,806,165 | B2 * | 11/2023 | Stepanek | A61B 5/251 |
| 2007/0255380 | A1 | 11/2007 | Meyer et al. | |
| 2013/0023749 | A1 * | 1/2013 | Afanasewicz | A61B 5/6885 604/173 |
| 2017/0281036 | A1 * | 10/2017 | Parvizi | A61B 5/291 |
| 2019/0232045 | A1 | 8/2019 | Kaib et al. | |
| 2019/0232071 | A1 | 8/2019 | Hulings et al. | |

OTHER PUBLICATIONS

International Search Report and Written Opinion of International Application No. PCT/US2021/038267 dated Sep. 23, 2021, 12 pp.

* cited by examiner

SENSOR INCLUDING ELECTRICALLY CONDUCTIVE MATERIAL CONTAINMENT ASSEMBLY

This application is a U.S. National Stage entry under 35 U.S.C. § 371 of International Application No. PCT/US2021/038267, filed Jun. 21, 2021, which claims priority from and the benefit of U.S. Provisional Patent Application Ser. No. 63/051,058, filed on Jul. 13, 2020, and entitled "SENSOR INCLUDING ELECTRICALLY CONDUCTIVE MATERIAL CONTAINMENT ASSEMBLY," the entire content of each of which is incorporated herein by reference.

TECHNICAL FIELD

The disclosure relates to medical sensors including electrodes.

BACKGROUND

Some medical monitors are configured to noninvasively monitor one or more physiological parameters of a patient using external electrodes. For example, a bispectral index (BIS) brain monitoring system is configured to monitor brain activity of a patient based on bioelectrical brain signals sensed via external electrodes (e.g., via an electroencephalogram (EEG)). The external electrodes can be applied to various anatomies of the patient (e.g., the temple and/or forehead). For example, some sensors for BIS monitoring may include a single strip that includes several electrodes for placement on the forehead to noninvasively acquire an EEG signal.

SUMMARY

The present disclosure describes devices, systems, and techniques for prolonging the shelf life sensors having one or more electrodes configured to monitor one or more physiological parameters of a patient, e.g., cardiac signals, brain signals, and the like. The sensors described herein include one or more electrodes configured to noninvasively sense a physiological parameter of a patient via electrical contact with the patient and an electrically conductive material that is configured to improve conductivity between the one or more electrodes and the patient and reduce the impedance of the electrode-to-patient connection. For example, the sensors may include an electrically conductive gel configured to be positioned between skin of a patient and an electrode, e.g., in an electrode well. The conductive gel may improve the surface area of contact between the electrode and the patient and reduce the impedance of an electrical path between the patient and the electrode.

In examples disclosed herein, an electrically conductive material (e.g., a conductive gel) is housed in a containment assembly. The containment assembly includes a deformable housing (e.g., a silicone bag) that defines one or more apertures through which the conductive material may flow. The containment assembly also includes one or more membranes configured to cover the one or more apertures prior to use of the sensor. For example, the one or more apertures may be positioned along an inner perimeter of the housing. The containment assembly is configured such that a relatively light force (also referred to herein as a pressure) on the containment assembly (directly or indirectly only a sensor of which the containment assembly is part) causes the conductive material to be released from the housing via the one or more apertures. The released conductive material may then flow out of the housing into a space between the electrode of the sensor and the patient, e.g., an electrode well, to help reduce the impedance of the electrode-to-patient connection.

The containment assembly may prolong the useful life of the electrically conductive material, thereby prolonging the useful life of a sensor including the electrically conductive material within the containment assembly. For example, the containment assembly can minimize or even prevent the electrically conductive material from drying out. In some examples, the containment assembly and, in some cases, the one or more membranes, may have a sufficiently low moisture vapor transmission rate (MVTR) to reduce and/or prevent drying of the conductive material.

In some examples, a sensor includes an electrode assembly having an electrode well; and a containment assembly comprising: a deformable housing configured to house an electrically conductive material, the housing being formed with one or more apertures; and at least one membrane configured, in an undeformed state of the housing, to cover at least one aperture of the one or more apertures to contain the electrically conductive material in the housing, wherein upon application of a sufficient force to the housing, the housing is configured to assume a deformed state in which the at least one membrane is configured to at least partially uncover the at least one aperture to enable the electrically conductive material to be released from the housing and into the electrode well through the at least partially uncovered at least one aperture.

In some examples, a sensor includes an electrode assembly having an electrode well; and a containment assembly comprising: a deformable housing configured to house an electrically conductive material, the housing having a toroidal shape and being formed with a plurality of apertures distributed along an inner perimeter of the housing; and a plurality of membranes, each membrane configured, in an undeformed state of the housing, to cover a respective aperture of the plurality of apertures, wherein each membrane of the plurality of membranes is configured to at least partially uncover the respective aperture upon the application of a sufficient force to the housing.

In some examples, a method includes: positioning a sensor on a surface, the sensor comprising: an electrode assembly having an electrode well; and a containment assembly configured to be positioned within the electrode well, the containment assembly comprising: a deformable housing configured to house an electrically conductive material, the housing being formed with one or more apertures; and at least one membrane configured, in an undeformed state of the housing, to cover at least one aperture of the one or more apertures; and applying a force to the sensor in a direction towards the surface, wherein the application of the force causes the at least one membrane to at least partially uncover the one or more apertures and causes the electrically conductive material to be released from the housing through the at least partially uncovered one or more apertures.

The details of one or more examples are set forth in the accompanying drawings and the description below. Other features, objects, and advantages will be apparent from the description and drawings, and from the claims.

DETAILED DESCRIPTION

Figure 1:
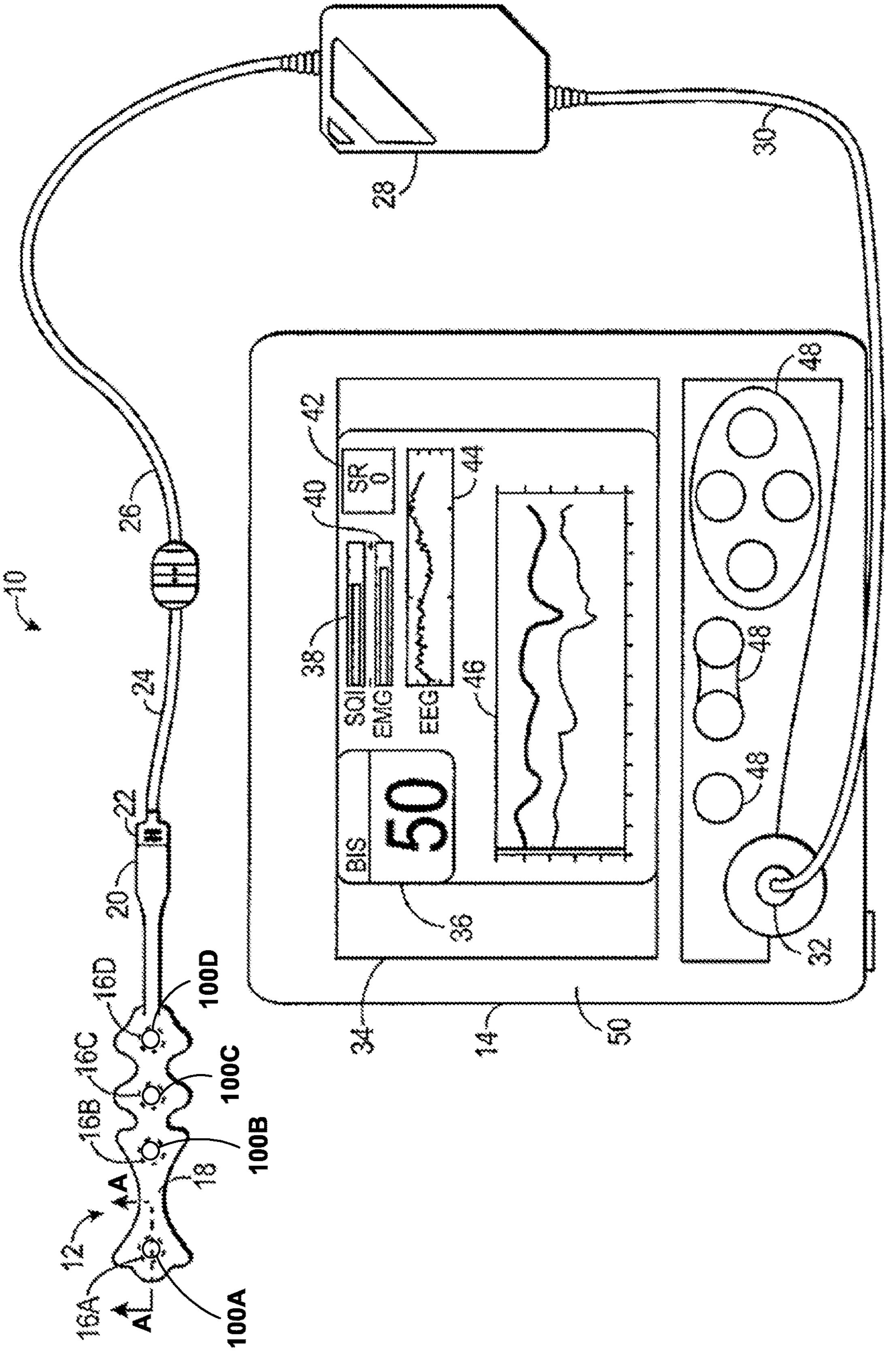
FIG. 1 is a conceptual block diagram illustrating an example monitoring system configured to be used with a sensor.

The present disclosure describes devices, systems, and techniques for prolonging the shelf life of sensors including one or more electrodes configured to sense one or more physiological parameters of a patient, e.g., cardiac signals, brain signals, and the like, and an electrically conductive material that is configured to improve an electrical connection between the electrodes and the patient. For example, the electrically conductive material is configured such that when it is positioned between a patient's skin and the electrodes, the material reduces the impedance of an electrical pathway between the electrodes and the patient, referred to herein as an electrode-to-patient connection. In addition, the electrically conductive material can help increase the surface area of contact between the electrode and the patient.

In examples disclosed herein, the electrically conductive material is housed in a containment assembly. The containment assembly includes a deformable housing (e.g., a silicone bag) that is formed with (e.g., defines) one or more apertures through which the electrically conductive material may flow. The containment assembly also includes one or more membranes configured, e.g., in an undeformed state of the housing, to cover the one or more apertures prior to use of the sensor. For example, the one or more apertures may be positioned along an inner perimeter of the housing, and in some examples may be distributed, equally or unequally, along the inner perimeter. In some examples, the containment assembly is sized to contain an appropriate amount of electrically conductive material to fill an electrode well of an electrode. For example, the containment assembly may have a toroidal shape and fit within the electrode well.

The containment assembly is configured such that the one or more membranes are configured to enable the electrically conductive material to be released from the housing through the one or more apertures, e.g., upon application of a sufficient force on the sensor in a direction towards a surface on which the sensor is positioned, which results in a relatively light pressure on the containment assembly. For example, the membrane(s) may be attached to the housing of the containment assembly, via extrusion, welding, an adhesive, or the like. A relatively light force applied to the sensor, such as a minimum pressure sufficient to adhere the sensor to a surface of the patient, may exert a downward force on the containment assembly, e.g., in a direction perpendicular to the electrode surface, which may depress the containment assembly housing and cause an increase in pressure within the containment assembly. The pressure within the containment assembly may be high enough to cause the one or more membranes to at least partially detach and/or rupture, thereby enabling the conductive material to flow out of the containment assembly housing through the one or more apertures, e.g., openings, previously covered by the one or more membranes. For example, upon application of a sufficient force, the housing may be configured to assume a deformed state in which the at least one membrane at least partially uncovers the one or more apertures. The conductive material may flow into a space between the electrode and the patient to help reduce the impedance of the electrode-to-patient connection.

A containment assembly may prolong the useful life of an electrically conductive material of a sensor, thereby prolonging the useful life of the sensor. For example, the containment assembly can minimize or even prevent the conductive material from drying out. In some examples, the containment assembly may have a sufficiently low moisture vapor transmission rate (MVTR) to reduce and/or prevent drying of the conductive material.

FIG. 1 is a conceptual block diagram illustrating an example monitoring system 10. In the example shown in FIG. 1, monitoring system 10 includes sensor 12 and electroencephalogram (EEG) monitor 14. Sensor 12 includes one or more electrodes 16 (e.g., four electrodes 16A, 16B, 16C, and 16D as shown in FIG. 1, but can include one electrode, two electrodes, three electrodes, or more than four electrodes in other examples). In other examples, monitor 14 can be configured to monitor one or more other physiological parameters of a patient instead of or in addition to EEG signals, such as, but not limited to, electrocardiogram (ECG) signals. Thus, while electrodes 16 are primarily referred to herein as being configured to acquire EEG signals, in other examples, electrodes 16 can be configured to sense other physiological parameters of a patient in other examples.

Electrodes 16 may have any suitable configuration. In some examples, electrodes 16 include a printed conductive ink supported within a flexible sensor body 18 to provide enhanced flexibility and conformance to patient tissue. In some examples, one or more of the electrodes 16 may be self-adherent and self-prepping, e.g., to temple and forehead areas of a patient. For example, electrodes 16 may include a series of protrusions and/or flexible tines. In some examples, the plurality of flexible tines includes tines similar to that in a ZipPrep™ electrode (Aspect Medical Systems of Framingham, Massachusetts, of which Medtronic plc is the parent entity). In some examples, the plurality of flexible tines may include a metal, an alloy, or a polymer. In some examples, the plurality of flexible tines includes a non-conductive composition, for example, nylon. In some examples, the plurality of tines may include a plastic material, such as a plastic backing and associated set of protrusions produced by modification (e.g., shaving) of a hook portion of a hook and loop fastener. The plurality of tines may prepare the patient for monitoring by penetrating the interface between the patient's skin and respective electrodes 16.

Sensor 12 further includes an electrically conductive material configured to increase the electrical conductivity between electrodes 16 and the patient, such as by lowering the impedance of an electrical path between electrodes 16 and the patient (e.g., skin of the patient). While the electrically conductive material is primarily referred to herein as an electrically conductive gel (or "conductive gel"), in other examples, the electrically conductive material can have any suitable configuration (e.g., viscosity). A gel may have sufficient viscosity to exhibit no flow when in the steady state (e.g., in the absence of an external force causing the gel to move) and may be particularly well suited to remain between electrodes 16 and a surface (e.g., skin of a patient).

Electrodes 16 may each be in, or at least partially define, an electrode well, as illustrated and described further below with respect to FIGS. 2-4. An electrode well of at least one of the electrode 16 includes a containment assembly within which a conductive gel is stored. The containment assembly is alternatively referred to herein as a gel containment assembly but can be configured to store an electrically conductive material in form other than a gel, such as a more liquid or solid form. In the example shown in FIG. 1, sensor 12 includes containment assemblies 100A, 100B, 100C, and 100D (generally referred to as a containment assembly 100) corresponding to electrodes 16A, 16B, 16C, and 16D and in respective electrode wells defined by electrodes 16A, 16B, 16C, and 16D. In other examples, however, only a subset of the electrodes 16 may include a containment assembly.

As discussed with reference to FIGS. 2A-6, sensor 12 is configured such that the conductive gel is releasable from containment assembly 100, such as during application of sensor 12 to a patient, by application of a downward force on sensor 12 (in a direction towards the patient when sensor 12 is being applied to a surface of the patient). When released from containment assembly 100, the conductive gel is configured to flow into a space between the respective electrode 16 and the surface of the patient to increase the electrical conductivity of a pathway between the electrodes and the patient. For example, the conductive gel (or other electrically conductive material) can be configured to flow into the space between the respective electrode 16 and the surface of the patient as the downward force is applied to sensor 12 and/or due to the fluid flow properties (e.g., viscosity) of the conductive gel.

Containment assembly 100 is configured to reduce and/or prevent the conductive gel from drying out. For example, containment assembly 100 can be formed from a material (e.g., silicone) that reduces moisture transmission out of containment assembly 100; moisture transmission out of containment assembly 100 can dehydrate the conductive gel stored in containment assembly 100, which may impact the electrical conductivity of the gel. In these ways, containment assembly 100 can be configured to extend the shelf life of sensor 12 and enable the conductive gel (or other electrically conductive material) to remain sufficiently hydrated to maintain its properties, such as electrical conductivity properties and/or fluid flow properties, over a longer period of time relative to examples in which the conductive gel is not stored in containment assembly 100.

Sensor 12 is configured to electrically connect to monitor 14. In the example shown in FIG. 1, sensor 12 includes a paddle connector 20, which couples through a connector 22 to a cable 24 (e.g., a patient interface cable), which in turn may be coupled to a cable 26 (e.g., a pigtail cable). In other examples, sensor 12 may be coupled to cable 26 thereby eliminating cable 24. Cable 26 may be coupled to a digital signal converter 28, which in turn is coupled to cable 30 (e.g., a monitor interface cable). In some examples, the digital signal converter 28 may be embedded in monitor 14 to eliminate cables 26 and 30. Cable 26 may be coupled to monitor 14 via a port 32 (e.g., a digital signal converter port). Sensor 12 can be electrically connected to monitor 14 using other techniques/configurations in other examples.

In some examples, monitor 14 is configured to monitor one or more physiological parameters of a patient via sensor 12. For example, sensor 12 may be a bispectral index (BIS) sensor 12 and monitor 14 may be configured to monitor brain activity of the patient based on EEG signals received from electrodes 16 of sensor 12. Monitor 14 includes processing circuitry configured to of algorithmically determine a bispectral index from the EEG signals, which may indicate a level of consciousness of a patient during general anesthesia.

In the example shown in FIG. 1, monitor 14 includes display 34 configured to display information, such as, but not limited to, sensed physiological parameters, historical trends of physiological parameters, other information about the system (e.g., instructions for placement of sensor 12 on the patient), and/or alarm indications. For example, monitor 14 may display a BIS value 36, a signal quality index (SQI) bar graph 38, an electromyograph (EMG) bar graph 40, a suppression ratio (SR) 42, an EEG waveform 44, and/or trends 46 over a certain time period (e.g., one hour) for EEG, SR, EMG, SQL and/or other parameters. BIS value 36 represents a dimensionless number (e.g., ranging from 0, i.e., silence, to 100, i.e., fully awake and alert) output from a multivariate discriminate analysis that quantifies the overall bispectral properties (e.g., frequency, power, and phase) of the EEG signal. SQI bar graph 38 (e.g., ranging from 0 to 100) indicates the signal quality of the EEG channel source (s) based on impedance data, artifacts, and other variables. EMG bar graph 40 (e.g., ranging from 30 to 55 decibels) indicates the power (e.g., in decibels) in a particular frequency range that includes power from muscle activity and other high-frequency artifacts. SR 42 (e.g., ranging from 0 to 100 percent) represents the percentage of epochs over a given time period (e.g., the past 63 seconds) in which the EEG signal is considered suppressed (i.e., low activity). In some examples, monitor 14 may display a verification screen verifying the proper placement of each electrode 16 of sensor 12 on the patient.

Additionally, monitor 14 may include various activation mechanisms 48 (e.g., buttons and switches) to facilitate management and operation of monitor 14. For example, monitor 14 may include function keys (e.g., keys with varying functions), a power switch, adjustment buttons, an alarm silence button, and so forth, which can be provided by buttons or by a touchscreen display 34.

Although one specific example monitor 14 is described with reference to FIG. 1, in other examples, sensor 12 can be used with other types of monitors.

Figure 2B:
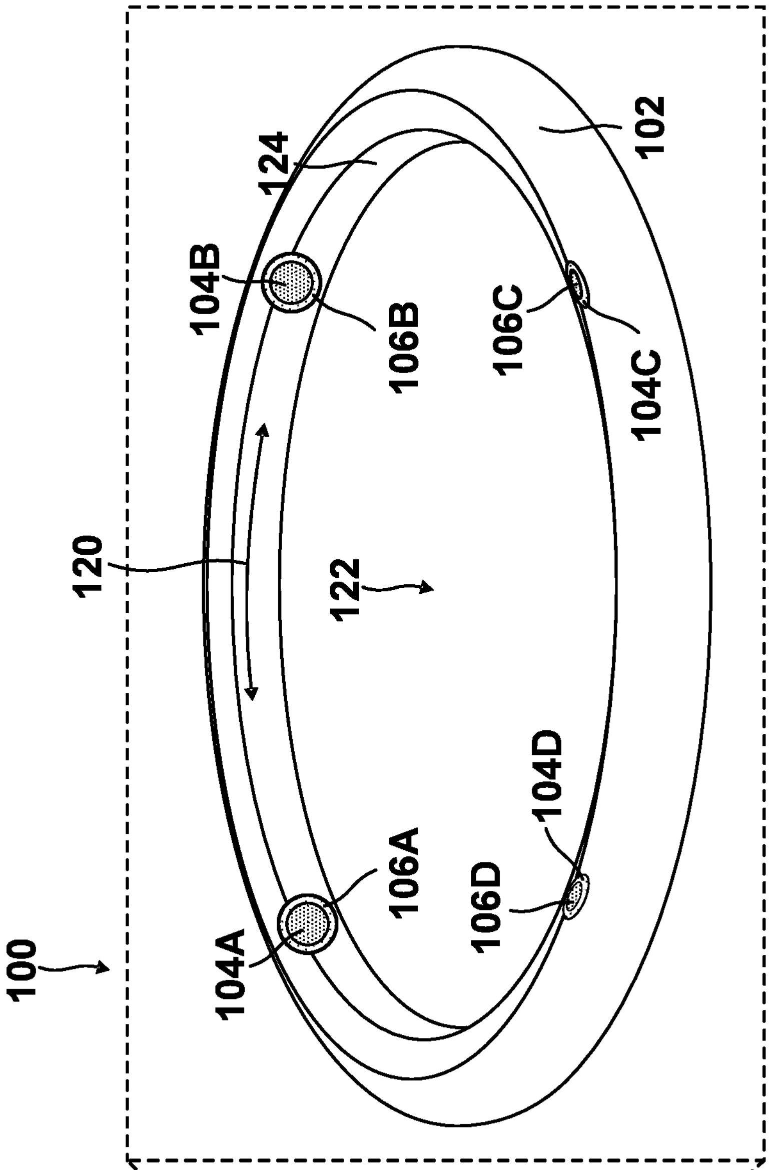
FIG. 2B is a perspective view of an example containment assembly.
Figure 2A:
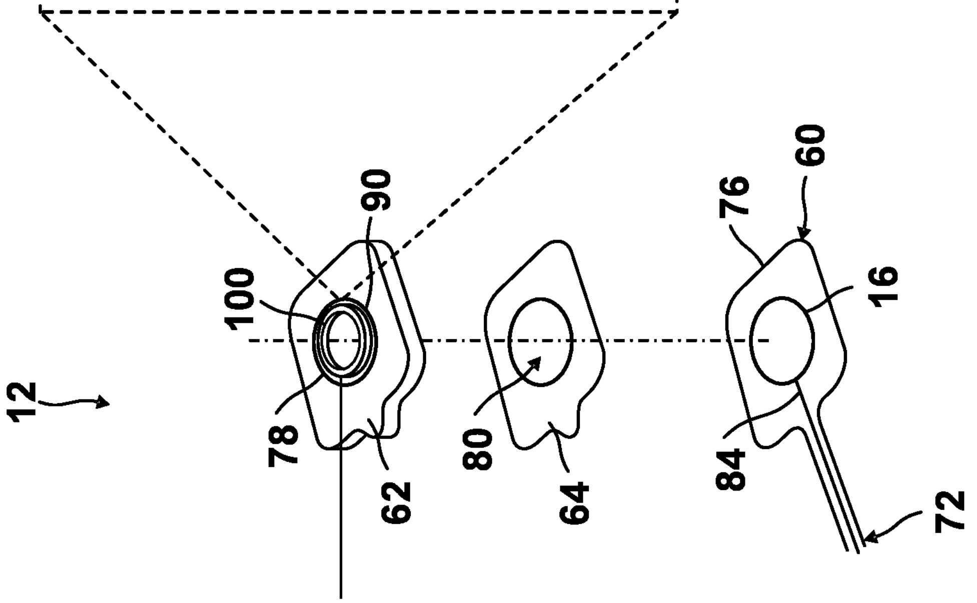
FIG. 2A is an exploded perspective view of an example of a sensor including a containment assembly configured to house an electrically conductive material.

FIG. 2A is an exploded perspective view of an example sensor 12 including a containment assembly 100 configured to contain an electrically conductive material. Electrode 16 is any example of electrodes 16A-16D shown in FIG. 1. In some examples, as shown in FIG. 2A, sensor 12 includes base layer 60, foam layer 62, and first adhesive 64 configured to secure foam layer 62 to base layer 60. In some examples, sensor 12 may include a patient contacting adhesive configured to secure sensor 12 to a patient. The patient contacting adhesive may be located on the opposite side of foam layer 62 from first adhesive 64. Base layer 60 may be constructed from any flexible polymeric material suitable for use in medical devices, such as, but not limited to, polyester, polyurethane, polypropylene, polyethylene, polyvinylchloride, acrylics, nitrile, PVC films, acetates, or similar materials that facilitate conformance of sensor 12 to the patient. Foam layer 62 may be relatively rigid compared to base layer 60 to provide padding and additional comfort to the patient. As an example, foam layer 62 may include any foam material suitable for use in medical applications, such as, but not limited to, polyester foam, polyethylene foam, polyurethane foam, or the like.

In the example shown, base layer 60 of sensor 12 includes an electrode portion 76, which is configured to facilitate retention of sensor 12 on a patient, e.g., to maintain pressure of corresponding electrode 16 positioned on electrode portion 76 against the patient's forehead, temple, or other external surface. Electrode 16 is positioned on electrode portion 76 of base layer 60, e.g., at the center of electrode portion 76 as shown in FIG. 2A or a non-centered location in other examples. The shape of electrode portion 76 may also be reflected in the shape of the foam layer 62 and first adhesives 64, and, more specifically, the portions of the foam layer 62 and first adhesives 64 that may attach to corresponding electrode portion 76 of base structural layer 60. Foam layer 62 and first adhesives 64 may also include respective holes 78 and 80 corresponding to the position of electrode 16 to facilitate electrical contact with the patient.

In some examples, foam layer 62, first adhesive 64, and a patient contacting adhesive may be provided as discrete layers as illustrated or may be provided as a single piece. That is, foam layer 62, first adhesive 64, and a patient contacting adhesive may be provided as a double-coated foam layer. Foam layer 62, first adhesive 64, and base layer 60 may form an electrode well, as further described and illustrated below with respect to FIGS. 3 and 4.

Electrode 16 includes an electrically conductive material. For example, electrode 16 may be formed from flexible conductive materials, such as one or more conductive inks. In some examples, electrode 16 may be produced by printing (e.g., screen printing or flexographic printing) a conductive ink on base layer 60 and allowing the ink to dry and/or cure. In some examples, the ink may be thermally cured. Sensor 12 may also include a plurality of conductors 84 disposed (e.g., screen or flexographically printed) on base layer 60 and configured to transmit signals to and from electrode 16 and to enhance flexibility of sensor 12, for example, as electrical connections to electrode 16. Conductors 84 may be formed from the same or a different conductive ink than electrode 16.

Suitable conductive inks for electrode 16 and conductors 84 may include inks having one or more conductive materials such as metals (e.g., copper (Cu) or silver (Ag)) and/or metal ions (e.g., silver chloride (AgCl)), filler-impregnated polymers (e.g., polymers mixed with conductive fillers such as graphene, conductive nanotubes, metal particles), or any ink having a conductive material capable of providing conductivity at levels suitable for performing physiological, EEG, and/or other electrical measurements. As an example, electrode 16 and/or conductors 84 may be formed from an ink having a mixture of Ag and AgCl. In some examples, silver and salts thereof (e.g., Ag/AgCl) may be desirable to use for electrode 16 and conductors 84 due to its enhanced stability (e.g., compared to copper and copper salts) during certain medical procedures, such as defibrillation. For example, the Ag/AgCl may enable the sensor to depolarize within a desired amount of time (e.g., seconds rather than minutes). This depolarization within a short amount of time may enable sensor 12 to be used a short time after the defibrillation or similar procedure. Generally, any suitable conductive material may be used for electrode 16 and the conductors 84.

In other examples, instead of or in addition to including a portion printed on base layer 60, electrode 16 and/or conductors 84 are separate from base layer 60 and attached to base layer 60.

Conductors 84, as noted above, are generally configured to transmit signals to and/or from electrode 16. In some examples, conductors 84 may be configured transmit signals such as power, data, and the like, collected at and/or transmitted to electrode 16. In the example shown, base layer 60 may include a tail portion 72 onto which conductors 84 may be formed to extend from electrode 16, for example, as a data and/or power connection and/or interface. Tail portion 72 may be a flat, flexible protrusion from base structural layer 60 to enable sensor 12 to be worn by the patient with minimal discomfort by reducing the bulk and weight of sensor 12 on the patient.

In some examples, tail portion 72 and conductors 84 may connect with paddle connector 20, illustrated and described above, thereby providing an electrical and structural interface between sensor 12 and monitor 14 of FIG. 1. As an example, paddle connector 20 may be configured to enable sensor 12 to clip into a connection point of monitor 14. Paddle connector 20 may also include a memory unit configured to store information relating to sensor 12, and to provide the stored information to monitor 14. For example, the memory unit may store code configured to provide an indication to monitor 14 as to the make/model of sensor 12, the time-in-operation of sensor 12, or the like. Alternatively or additionally, the memory unit may include code configured to perform a time-out function where sensor 12 is deactivated after a predetermined number of connections, time-in-operation, or similar use-related metric. In some examples, the memory unit may also store patient-specific and/or sensor-specific information such as trend data collected by electrode 16, calibration data related to electrode 16 and/or conductors 84, and the like. In other words, the memory unit may be configured to enable sensor 12 to be used in conjunction with monitor 14 for the collection of patient data.

Sensor 12 may be kept in electrical contact with a patient for the collection of physiological data or similar data. Sensor 12 includes an electrically conductive gel configured to facilitate the transmission of electrical signals between electrode 16 and the patient tissue. In some examples, the conductive gel may include a wet gel or a hydrogel that is compatible with the materials used for electrode 16 and conductors 84. For example, the conductive gel may include a salt (e.g., sodium chloride (NaCl) or potassium chloride (KCl)) having an ionic concentration suitable for conducting electrical signals between the patient and electrode 16. For example, the concentration of chloride ions in the conductive gel may be between approximately 2 and 10% by weight.

Prior to use of sensor 12, the conductive gel is housed in containment assembly 100, which, in the example shown in FIG. 2A, is positioned within an electrode well 90 of electrode 16. Electrode well 90 is, for example, a volume of spaced defined by one or more surfaces of sensor 12. In some examples, as shown in FIG. 1, electrode 16 defines a first surface of electrode well 90 and an opposite side of electrode well 90 from electrode 16 is open. This open side of electrode well 90 is configured to face a patient when sensor 12 is properly applied to the patient. In other examples, electrode well 90 can have another configuration.

FIG. 2B is a perspective view of an example containment assembly 100, which includes housing 102 formed with a plurality of apertures 104, and a plurality of membranes 106. Housing 102 defines an internal volume (e.g., a space) in which an electrically conductive gel (or other electrically conductive material) is configured to be housed. For example, housing 102 may fully surround the electrically conductive gel except where apertures 104 are defined. Housing 102 may be made of any material having sufficiently low MVTR to reduce/prevent drying of the conductive gel while it is contained in the internal volume defined by housing 102. In addition, housing 102 is at least partially deformable and flexible, having sufficient flexibility to allow an increase in internal pressure in the internal volume upon the application of a force compressing housing 102, e.g., such as during application of sensor 12 to a patient. In some examples, housing 102 may be formed from silicone, nylon, flexible polymers, and the like. The material of housing 102 is selected to be thin and flexible, such that housing 102 is deformable. In the example shown in FIG. 2B, housing 102 is configured to fit within electrode well 90.

In the example shown, housing 102 has a plurality of apertures 104A, 104B, 104C, and 104D (collectively referred to as apertures 104 or individually referred to as an aperture 104). Although four apertures 104 are shown in the example of FIG. 2B, in other examples, housing 102 may have a fewer or a greater number of apertures. Apertures 104 define openings into the internal volume of housing 102 that contains the conductive gel and defines passageways through which the conductive gel may exit housing 102. In the example shown in FIGS. 2A and 2B, apertures 104 are located along inner perimeter 120 of housing 102 such that the conductive gel may be released through apertures 104 into space 122 defined by inner perimeter 120. The space 122 is within electrode well 90 in the example shown in FIGS. 2A and 2B.

Apertures 104 have any suitable shape and size that enables the conductive gel to exit housing 102, e.g., enables a sufficient amount (e.g., a majority) of the conductive gel to exit the housing 102 in a reasonable amount of time (e.g., a few seconds or less, such as about one second) in response to a downward force applied to sensor 12 when sensor 12 is placed on a patient. In some examples, the size of each aperture 104 is selected based on the number of apertures of housing 102 (e.g., there may be fewer larger apertures or a greater number of relatively smaller apertures), based on the viscosity of the conductive gel, and/or a combination thereof. In some examples, the size of each aperture 104 may be selected based on a ratio of the total open area of apertures 104 to inner surface area 124 of housing 102 along inner perimeter 120 adjacent to space 122. Inner surface area 124 may be the inner half of the total surface area of housing 102. In some examples, the total open area defined by apertures 104 may be configured to be 5% and 25% of inner surface area 124, such as 8% to 20% of inner surface area 124, such as 8% and 15% of inner surface area 124, or 10% of inner surface area 124.

In the example shown, apertures 104 are substantially circular. In other examples, apertures 104 may be any other shape, for example, square, triangular, a pair of crossed slits, a single slit, and the like or combinations thereof. For example, two or more of the apertures 104 may have different shapes in some examples. In other examples, apertures 104 have the same shape.

In some examples, apertures 104 are equally spaced along the circumference of inner perimeter 120 of housing 102 and/or symmetrically distributed along inner perimeter 120. In some examples, a symmetrical arrangement of apertures 104 may enable a conductive gel disposed within housing 102 to be applied substantially evenly over electrode 16. In some examples, apertures 104 may have an unequal spacing, and may be located at any position on housing 102.

Sensor 12 includes one or more membranes 106 configured to cover apertures 104 to help contain the conductive gel within the interior volume defined by housing 102. For example, in the example shown in FIG. 2B, sensor 12 includes a plurality of membranes 106, e.g., membranes 106A, 106B, 106C, and 106D covering respective apertures 104A, 104B, 104C, 104D. In some examples, one or more membranes 106 are configured to cover apertures 104 when housing 102 is in an undeformed state. In the example shown, a portion of a surface of membranes 106 are configured to attach to housing 102 (e.g., via an adhesive, welding, thermal bonding, or another suitable technique). In other examples, membranes 106 may cover apertures 104 via any other means, for example, by negative pressure within housing 102.

Membranes 106 may be made of any material with sufficiently low MVTR and able to sufficiently seal apertures 104 from moisture and/or gel transmission through apertures 104. In some examples, membranes 306 may be formed from silicone.

Membranes 106 are configured to uncover apertures 104 thereby releasing a conductive gel contained therein. In some examples, membranes 106 are configured to enable an electrically conductive material to be released from housing 102 through one or more of apertures 104 upon application of a sufficient force to housing 102 (e.g., in response to the force). For example, the sufficient can be a force and/or pressure applied to sensor 12 towards a patient to adhere sensor 12 to the patient; such a force and/or pressure may deform housing 102 within electrode well 90 and increase an internal pressure within housing 102 sufficient to cause membranes 106 to rupture, detach, or otherwise uncover apertures 104. In some examples, membranes 106 are configured to be breached in response to the force applied by the electrically conductive material in housing 102 being pushed through apertures 104, thereby allowing the electrically conductive material to be released from housing 102 through apertures 104. In some examples, housing 102 is configured to assume a deformed state in response to the application of the sufficient force, the deformed state being a state in which membranes 106 may be configured to at least partially uncover apertures 104 to enable the electrically conductive material to be released from housing 102 into electrode well 90 through apertures 104.

In some examples, membranes 106 may be configured rupture, detach, be breached, or otherwise uncover apertures 104 upon application of a force to sensor 12 that is greater than 0.1 Newton (N), for example, a 0.1 to 3 N force. That is, the sufficient force can be 0.1 Newton (N), for example, a 0.1 to 3 N force. In some examples, membranes 106 may be configured rupture, detach, be breached, or otherwise uncover apertures 104 upon application of a 1 N to 2 N force to sensor 12. In the example shown, membranes 106 are substantially circular (e.g., circular or nearly circular to the extent permitted by manufacturing tolerances). In other examples, membranes 106 may be any other shape, e.g., square, triangular, rectangular, and the like. In some examples, smaller apertures 104 may require a lower pressure within housing 102 to cause membranes 106 to rupture, detach, or otherwise uncover apertures 104, and equivalently requiring a lower pressure and/or force applied to housing 102.

In some examples, housing 102 may be configured to rupture and release the conductive gel contained therein upon application of a force to sensor 12. For example, housing 102 may rupture in addition to, or in lieu of, membranes 106 rupturing, detaching, or otherwise uncovering apertures 104, upon application of a force to sensor 12 that is greater than 0.1 N, such as between 0.1 N to 3 N, or between 1 N to 2 N.

Figure 3:
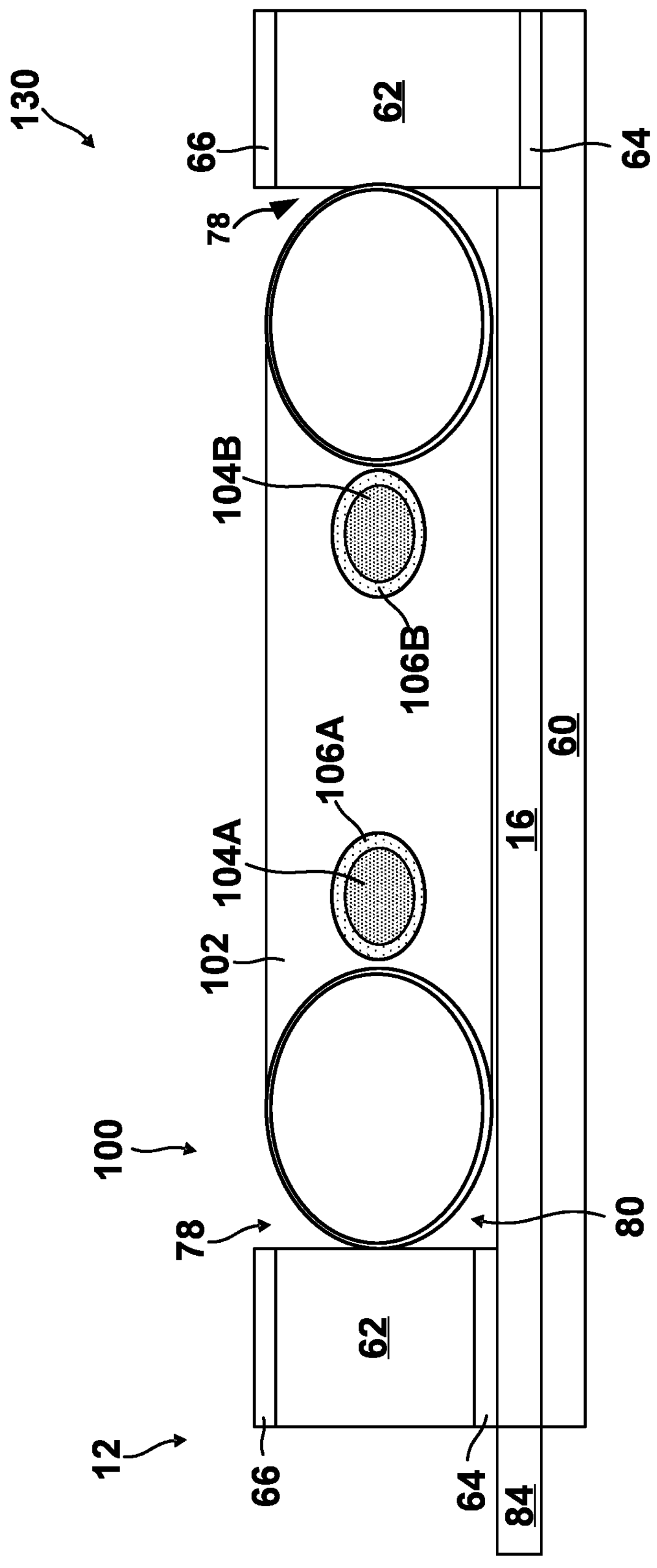
FIG. 3 is cross-sectional view of part of the sensor of FIG. 1 taken along line A-A in FIG. 1 and illustrates an example electrode well before application of the sensor to a patient.

FIG. 3 is cross-sectional view of sensor 12 taken along line A-A in FIG. 1 and illustrates an example electrode well

90 of sensor 12 before application of sensor 12 to a patient. In the example shown, sensor 12 includes electrode assembly 130 having electrode well 90. Electrode assembly 130 may include electrode 16, foam layer 62, base structural layer 60, first adhesive 64, patient contacting adhesive 66, containment assembly 100, and conductors 84. Electrode well 90 may be formed by components of sensor 12 and/or electrode assembly 130, such as electrode 16 and foam layer 62. In the example shown in FIG. 3, foam layer 62 may be adhered to electrode 16 and/or base structural layer 60 via first adhesive 64. Foam layer 62 and first adhesive 64 may define holes 78 and 80, respectively (FIG. 2A), which are configured to be aligned with each other. In the example shown, electrode 16 defines the bottom of electrode well 90, and foam layer 62 and first adhesive 64 define the sidewalls of electrode well 90. In the example shown, sensor 12 may include patient contacting adhesive 66, as described above.

Figure 4:
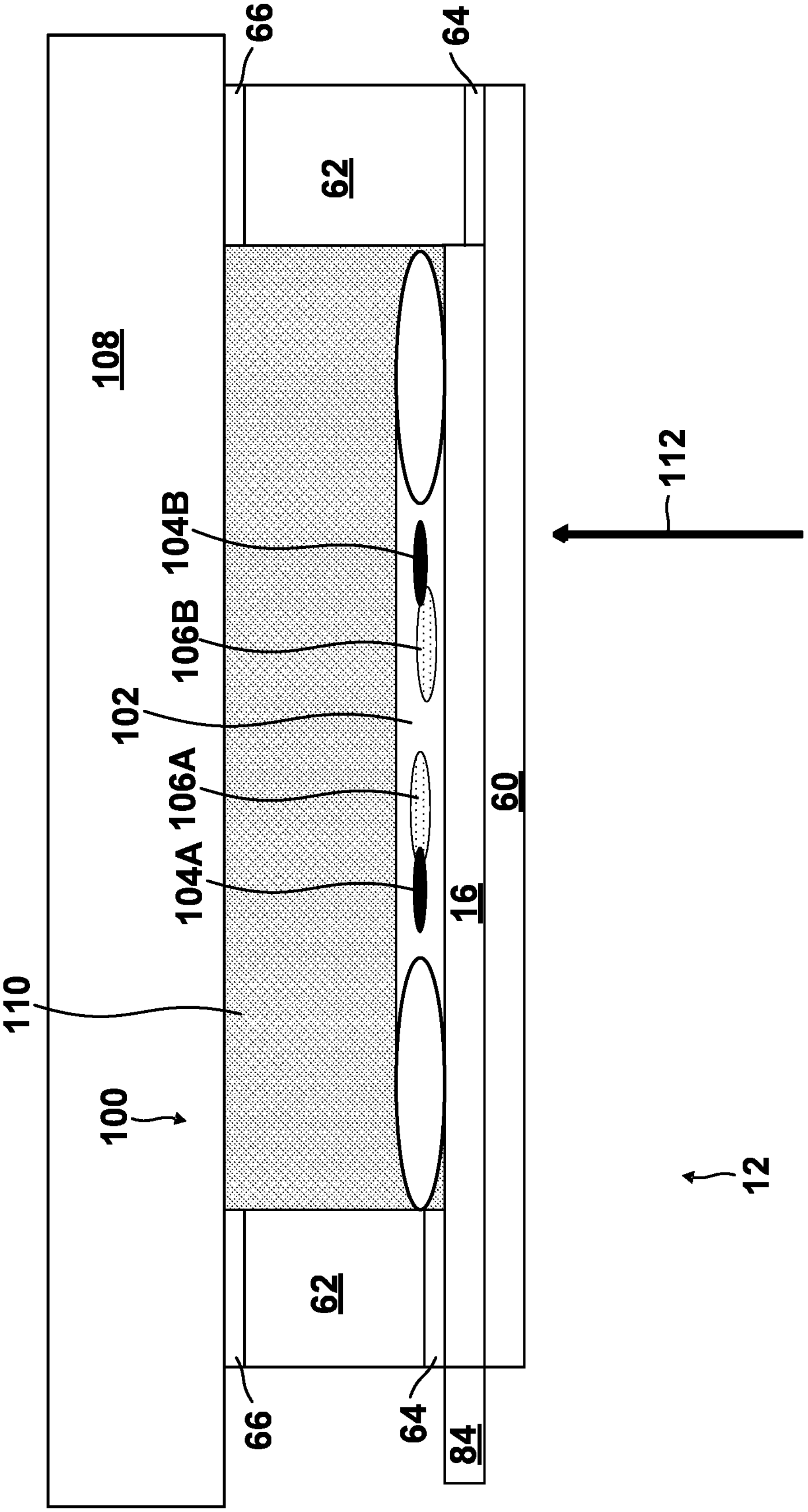
FIG. 4 is cross-sectional view of part of the sensor of FIG. 1 taken along line A-A in FIG. 1 and illustrates the example electrode well after application of the sensor to a patient.

In the example shown, containment assembly 100 is positioned in electrode well 90 such that the conductive gel, when released from housing 102, at least partially fills electrode well 90, as shown in FIG. 4. FIG. 4 is a cross-sectional view of sensor 12 taken along line A-A in FIG. 1 and illustrates electrode well 90 of sensor 12 after application of sensor 12 to surface 108 (e.g., a skin surface) of a patient. In the example shown, a force in direction 112 may be applied to sensor 12 in a direction towards patient surface 108 to apply sensor 12 to patient surface 108. The force may be sufficient to bring patient contacting adhesive 66 into engagement with patient surface 108 and adhere to patient surface 108. The force may compress and/or depress foam layer 62 in a direction towards patient surface 108, and in some examples, depress first adhesive 64 and patient contacting adhesive 66 as well and may compress and/or depress containment assembly 100 within electrode well 90. In some examples, the sidewalls of electrode well 90 defined by foam layer 62 may keep the outer perimeter of containment assembly 100 in place, e.g., the sidewalls may not allow containment assembly 100 to deform outwards, thereby causing the conductive gel to be pushed towards apertures 104. A pressure within an internal volume of housing 102 may increase due to the compression.

In some examples, the increased pressure within housing 102 of containment assembly 100 may rupture and/or detach membranes 106 from housing 102, thereby enabling conductive gel 110 to be released from housing 102 and into electrode well 90 through apertures 104. In the example shown, membranes 106A and 106B are detached and displaced from apertures 104A and 104B, and containment assembly 100 is in a compressed, depressed, and/or deflated state having released some or all conductive gel 110. As shown in FIG. 4, housing 102 may house enough gel 110 to fill a space between electrode 16 and patient surface 108 and enable gel 110 to complete an electrical pathway between electrode 16 and surface 108. Conductive gel 110 is more electrically conductive than air and may thus reduce an electrical impedance between electrode 16 and patient surface 108.

Figure 5:
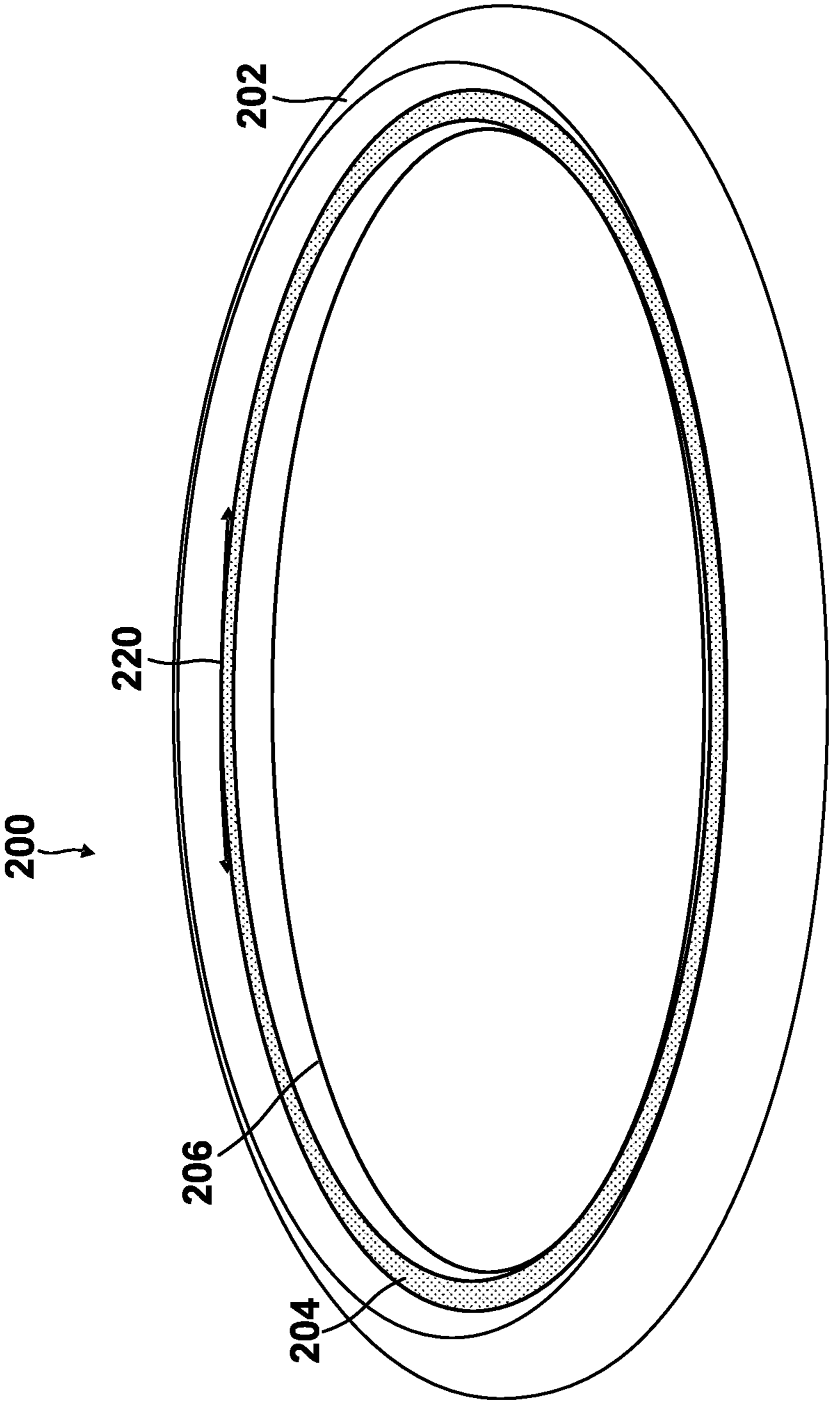
FIG. 5 is a perspective view of another example containment assembly.

In other examples, sensor 12 can include a containment assembly that has a different aperture configuration. In these examples, the containment assembly can be configured to release the conductive gel using any of the techniques described above with reference to FIGS. 1-4. FIG. 5 is a perspective view of another example containment assembly 200. In the example shown, containment assembly 200 includes deformable housing 202 defining an aperture 204, and membrane 206. Containment assembly 200 is substantially similar to containment assembly 100 illustrated and described above and having a different aperture and membrane configuration.

In the example shown, housing 202 defines a single aperture 204 that is a slot, or slit, along at least a portion of the inner perimeter 220 of housing 202. In other examples, aperture 204 may be located anywhere along a circumference of housing 202, e.g., the outer perimeter, or the top and/or bottom perimeter. In other examples, housing 202 may include more than one aperture 204, e.g., along each of the outer, inner, top, and bottom perimeters of housing 202.

In the example shown, membrane 206 adheres to housing 202 and prevents a conductive gel contained therein from releasing from housing 202. In other examples, membrane 206 may be welded to housing 202, integrally formed with housing 202, or may cover aperture 204 via any other means, for example, by negative pressure within housing 202. Membrane 206 may be made of any material with sufficiently low MVTR and able to sufficiently seal aperture 204 from moisture and/or gel transmission through aperture 204. In some examples, membrane 206 may be silicone. Membrane 206 may be configured to rupture or detach from housing 202 upon application of a force to a sensor 12 including containment assembly 200. In other words, membrane 206 may be configured to uncover aperture 204 and release a conductive gel contained therein. For example, a force applied to housing 202 may deform housing 202 and increase an internal pressure within housing 202 sufficient to cause membrane 206 to rupture, detach, or otherwise uncover aperture 204.

Figure 6:
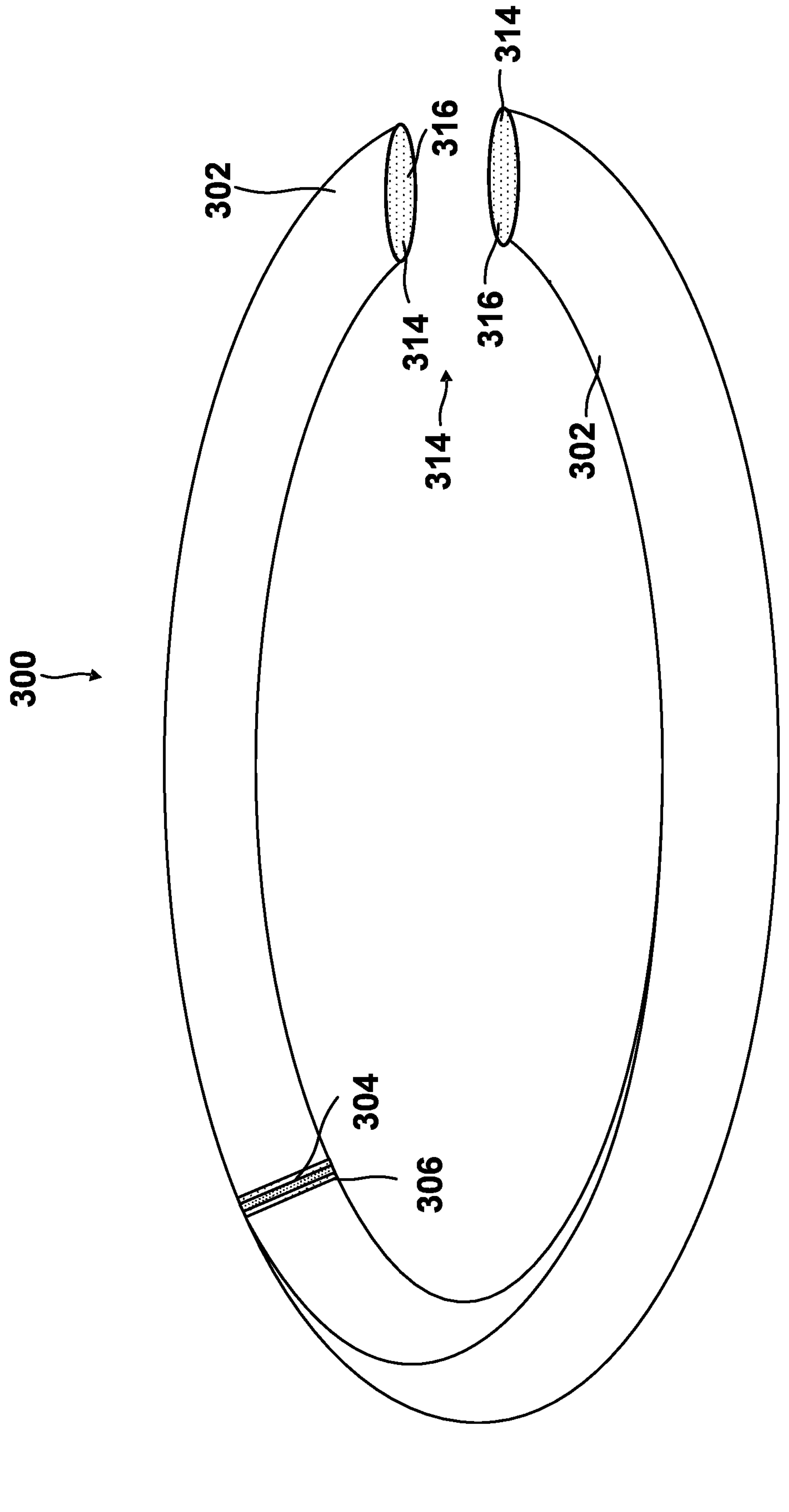
FIG. 6 is a perspective view of another example containment assembly.

FIG. 6 is a perspective view of another example containment assembly 300. In the example shown, containment assembly 300 includes housing 302, apertures 304 and 314, and membranes 306 and 316. Containment assembly 300 is substantially similar to gel containment assembly 100 illustrated and described above and having a different aperture and membrane configuration. In the example shown, two different aperture configurations are illustrated. In some examples, gel containment assembly 300 may include one or both of the aperture configurations alone or in combination, and in addition gel containment assembly 300 may include one or both of the illustrated aperture configurations illustrated in combination with any other aperture configuration, such as apertures 104, 204, or any other aperture configuration.

In some examples, deformable housing 302 includes an aperture 304 that is a slot, or slit, along at least a portion of the circumference of revolution of housing 302. For example, housing 302 may be a toroid, as illustrated, with an axis of revolution passing through the hole in the middle of the toroidal shape. The toroid may be described as a surface of revolution, e.g., a circle, a rectangle, a triangle, a polygon, and the like, that is rotated about the axis of revolution, the surface of revolution being the cross-sectional shape of the toroid. In other words, aperture 304 may be along at least a portion of the circumference of the surface of revolution of housing 302. In some examples, housing 302 may include a plurality of apertures 304.

In some examples, in addition to or instead of aperture 304, housing 302 includes apertures 314. As shown, apertures 314 may be endcaps of a housing 302, which is a noncontinuous toroid. In other words, housing 302 may be a toroid with a segment or length of the toroid removed, or housing 302 may be formed as a portion of a toroid omitting a segment and/or length.

In the example shown, membrane 306 adheres to housing 302 and prevents a conductive gel contained therein from releasing from housing 302 via aperture 304. In other examples, membrane 306 may be welded to housing 302, integrally formed with housing 302, or may cover aperture 304 via any other means, for example, by negative pressure within housing 302. In the example shown, membranes 316 adhere to housing 302 and prevents a conductive gel contained therein from releasing from housing 302 via apertures 314. In other examples, membranes 316 may be welded to housing 302, integrally formed with housing 302, or may cover apertures 314 via any other means, for example, by negative pressure within housing 302. Membranes 306 and 316 may be made of any material with sufficiently low MVTR and able to sufficiently seal apertures 304 and 314 from moisture and/or gel transmission through apertures 304 and 314. In some examples, membranes 306 and 316 may be silicone. Membranes 306 and 316 may be configured to rupture or detach from housing 302 upon application of a force to sensor 12. In other words, membranes 306 and 316 may be configured to uncover apertures 304 and 314 and release a conductive gel contained therein. For example, a force applied to housing 302 may deform housing 302 and increase an internal pressure within housing 302 sufficient to cause membranes 306 and 316 to rupture, detach, or otherwise uncover apertures 304 and 314.

Figure 7:
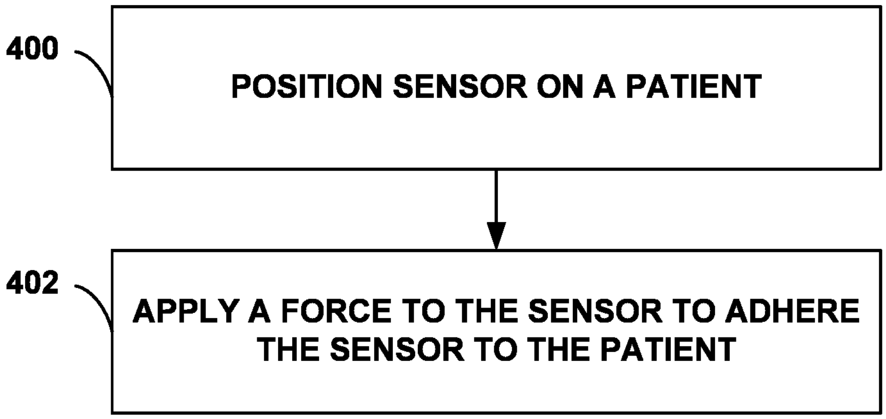
FIG. 7 is a flow diagram of an example method of using a sensor including a containment assembly configured to house an electrically conductive material.

FIG. 7 is a flow diagram of an example method of using a sensor including a containment assembly that houses an electrically conductive material that facilitates electrical coupling between an electrode of the sensor and a surface (e.g., a skin surface of a patient). While FIG. 7 is described with reference to sensor 12 and containment assembly 100, in other examples, the method can be used with other sensors and containment assemblies.

A user may position sensor 12 on a patient (400). For example, a user may position sensor 12 on patient surface 108 (FIG. 4), e.g., the skin surface, such that patient contacting adhesive 66 is closest to patient surface 108 (e.g., in directly contact with patient surface 108) and electrode 16 is furthest from patient surface 108. In some examples, a liner is positioned over patient contacting adhesive 66 prior to use of sensor 12 and the user may remove the liner before positioning sensor 12 on the patient to expose patient contacting adhesive 66. Adhesive can be, for example, a pressure sensitive adhesive.

The user may apply a force to adhere sensor 12 to the patient (402). For example, the user may apply sensor 12 to a patient surface 108 by applying a force in direction 112 (FIG. 4) towards patient surface 108 so as to adhere or otherwise affix the sensor to the patient, e.g., via patient contacting adhesive 66. The applied force to sensor 12 may exert a force on containment assembly 100 within electrode well 90 of sensor 12. The applied force may compress and/or depress containment assembly 100, thereby causing an increase in pressure within housing 102 of containment assembly 100. The pressure within housing 102 which may be large enough to rupture, detach, or otherwise cause one or more membranes 106 covering one or more apertures 104 defined by housing 102 to uncover the one or more apertures 104, thereby allowing a conductive gel contained in housing 102 to be exit housing 102 through uncovered apertures 104 and into electrode well 90. The conductive gel may extend between electrode 16 and patient surface 108 and increase the electrical conductivity between the patient and the electrode and reduce an impedance between patient surface 108 and electrode 16.

Various examples of the disclosure have been described. Any combination of the described systems, operations, or functions is contemplated. These and other examples are within the scope of the following claims.

What is claimed is:

1. A sensor, comprising:

an electrode assembly having an electrode well; and a containment assembly, positioned within the electrode well, comprising:

a deformable housing configured to house an electrically conductive material, the deformable housing being prevented from deforming outwardly while positioned within the electrode well, the deformable housing comprising:

a plurality of apertures positioned along an inner perimeter of the deformable housing; and at least one membrane configured to transition between an undeformed state and a deformed state, wherein the at least one membrane in the undeformed state is configured to cover at least one aperture of the plurality of apertures to contain the electrically conductive material in the deformable housing, wherein upon application of an amount of force to the deformable housing, the at least one membrane in the deformed state is configured to at least partially uncover the at least one aperture of the plurality of apertures to enable the electrically conductive material to be released from the deformable housing through the at least one aperture and into the electrode well.

2. The sensor of claim 1, wherein the deformable housing and the at least one membrane have a moisture vapor transmission that prevents drying of the electrically conductive material.

3. The sensor of claim 1, wherein the deformable housing comprises a silicone bag.

4. The sensor of claim 1, wherein the deformable housing has a toroidal shape.

5. The sensor of claim 1, wherein the plurality of apertures is one of distributed along an inner perimeter of the deformable housing or forms a slit extending along at least a portion of the inner perimeter of the deformable housing.

6. The sensor of claim 1, wherein the at least one membrane comprises a plurality of membranes, each membrane of the plurality of membranes configured to cover a respective aperture of the plurality of apertures, wherein upon the application of the amount of force the at least one membrane is configured to at least one of detach from the deformable housing or rupture to at least partially uncover the at least one aperture.

7. The sensor of claim 1, wherein upon the application of the amount of force the at least one membrane is configured to be breached, thereby allowing the electrically conductive material to be released from the deformable housing through the at least one aperture.

8. The sensor of claim 1, wherein the deformable housing defines an internal volume in which the electrically conductive material is housed.

9. The sensor of claim 1, wherein the electrode assembly comprises:

a backing layer;

at least one electrode disposed on the backing layer;

a foam layer disposed on at least a portion of the backing layer; and an adhesive disposed on at least a portion of the foam layer and configured to adhere the sensor to a patient, wherein the electrode well is defined by the foam layer and the backing layer.

10. The sensor of claim 1, wherein a size of one or more of the plurality of apertures is determined based on a ratio of total open area of the plurality of apertures in relation to an inner perimeter surface area.

11. The sensor of claim 6, wherein a size of one or more of the plurality of apertures is determined based on a ratio of total open area of the plurality of apertures in relation to an inner perimeter surface area.

12. The sensor of claim 6, wherein the plurality of apertures is arranged in a symmetrical arrangement.

13. The sensor of claim 6, wherein the plurality of apertures is not in a symmetrical arrangement.

14. A sensor, comprising:

an electrode assembly having an electrode well; and a housing configured to house an electrically conductive material, the housing being prevented from deforming outwardly while positioned within the electrode well, the housing comprising:

a plurality of apertures positioned along an inner perimeter of the housing; and at least one membrane configured to transition the housing between an undeformed state and a deformed state, wherein the at least one membrane in the undeformed state is configured to contain the electrically conductive material in the housing by covering at least one aperture of the plurality of apertures, and wherein in response to an amount of force the at least one membrane in the deformed state is configured to release the electrically conductive material from the housing into the electrode well by at least partially uncovering the at least one aperture of the plurality of apertures.

15. The sensor of claim 14, wherein the housing comprises a silicone bag.

16. The sensor of claim 14, wherein the housing has a toroidal shape.

17. The sensor of claim 14, wherein the at least one membrane comprises a plurality of membranes, and wherein each membrane of the plurality of membranes is configured to cover a respective aperture of the plurality of apertures.

18. The sensor of claim 14, wherein in response to the amount of force the at least one membrane in the deformed state is configured to at least one of rupture or detach from the housing to at least partially uncover the at least one aperture.

19. The sensor of claim 14, wherein the amount of force is dependent on a plurality of sizes of the plurality of apertures.

20. The sensor of claim 14, wherein the electrode assembly comprises:

a backing layer;

at least one electrode disposed on the backing layer; and a foam layer disposed on at least a portion of the backing layer, wherein the electrode well is defined by the foam layer and the backing layer.

* * * * *